United States Patent
Wang et al.

(10) Patent No.: US 8,299,937 B2
(45) Date of Patent: Oct. 30, 2012

(54) SELF-POWERED IN-PIPE FLUID METER AND PIPING NETWORK COMPRISING A PLURALITY OF SUCH FLUID METERS

(75) Inventors: Zhenfeng Wang, Singapore (SG); Ser Youn Lim, Singapore (SG); Wei Fan, Singapore (SG); Danhong Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 637 days.

(21) Appl. No.: 12/376,733

(22) PCT Filed: Aug. 6, 2007

(86) PCT No.: PCT/SG2007/000236
§ 371 (c)(1),
(2), (4) Date: Dec. 1, 2009

(87) PCT Pub. No.: WO2008/018836
PCT Pub. Date: Feb. 14, 2008

(65) Prior Publication Data
US 2010/0085211 A1 Apr. 8, 2010

Related U.S. Application Data

(60) Provisional application No. 60/836,257, filed on Aug. 7, 2006.

(51) Int. Cl.
*G08B 23/00* (2006.01)
(52) U.S. Cl. .............. 340/870.02; 422/68.1; 210/747.1
(58) Field of Classification Search ............. 422/68.1; 210/747.1
See application file for complete search history.

(56) References Cited

U.S. PATENT DOCUMENTS

| | | | | |
|---|---|---|---|---|
| 6,221,257 | B1 * | 4/2001 | Grim | 210/747.1 |
| 6,444,172 | B2 * | 9/2002 | Fukunaga et al. | 422/68.1 |
| 2003/0167919 | A1 | 9/2003 | Schempf | |

FOREIGN PATENT DOCUMENTS

| | | |
|---|---|---|
| FR | 2653554 | 4/1991 |
| JP | 2002267510 | 9/2002 |
| WO | 2005/015789 | 2/2005 |
| WO | 2007/076039 | 7/2007 |

* cited by examiner

Primary Examiner — Jean B Jeanglaude
(74) Attorney, Agent, or Firm — Altera Law Group, LLC

(57) ABSTRACT

A self-powered in-pipe fluid meter to be mounted inside of a pipe carrying a fluid therein. The fluid meter comprises at least one sensing unit capable of measuring one or more parameters of the fluid inside of the pipe; a telemetric data transmission unit capable of telemetrically transmitting data including a measured fluid parameter to a host terminal and/or another fluid meter; and at least one fluid-driven power source unit capable of generating power from the fluid flow within the pipe and supplying power to the sensing unit and/or the transmission unit.

9 Claims, 2 Drawing Sheets

SELF-POWERED IN-PIPE FLUID METER AND PIPING NETWORK COMPRISING A PLURALITY OF SUCH FLUID METERS

CROSS-REFERENCE TO RELATED APPLICATIONS

The present invention claims the benefit of priority of U.S. provisional application No. 60/836,257 filed Aug. 7, 2006, the contents of which is hereby incorporated by reference in its entirety for all purposes.

FIELD OF THE INVENTION

The present invention relates to fluid meters such as a water quality meter used for monitoring the quality of water in water pipes of a water transmission piping network.

BACKGROUND OF THE INVENTION

Historically, the monitoring of water quality in water transmission and distribution systems has been done through the discrete sampling of particular sites of interest and at random intervals. The samples collected are usually processed off-line through wet-chemistry methods. The processing often takes place several days or weeks after the sample has been gathered. Accordingly, there may be some instances where the degradation in the water quality is only apparent after the change in water quality has caused human illness and/or environmental changes.

Within the last few years, breakthroughs in sensor technology have largely shortened the time required for measurement of the various parameters that dictate the quality of a fluid such as water. The required time for the measurement of such parameters has been reduced into minutes or seconds. Furthermore, the measurement of multiple parameters has been integrated into portable sensor modules. The rapidly maturing technologies in the areas of telecommunication and Internet systems also provide long-distance telemetry solutions for the online monitoring of the quality of water in a water distribution network.

However, there exist several problems with the presently used sensors. Water distribution monitoring networks typically comprise a host station and remote sensors. Electrical power is required for the remote sensors so that they can perform functions like sensing, signal conditioning, data logging and data transmission towards the host station. In reality, the location of water distribution networks and their respective pipe lines are not always close to electricity supply networks. In such cases, the remote sensors have to be self-powered. Some known methods for powering up the remote sensors include using batteries and solar cells. The drawbacks of these power sources are that the batteries need to be recharged or replaced due to their very limited lifespan and solar cells can only work properly under restricted environmental and weather conditions.

As for methods of data transmission between the host terminal and remote sensors, said methods include cellular telephone, GPS satellite, Internet or intranet. For all these methods, the remote sensor must be equipped with a modem and/or an antenna, which means, the remote sensor has to be exposed to the elements as it may include an on-surface module, that is, a module provided on the outer surface of a pipe. The drawback here is that such an on-surface module needs to be protected and regularly surveilled, which then introduces significant manpower costs for the monitoring of water distribution networks having large numbers of remote sensors.

The present invention seeks to overcome the aforesaid problems and difficulties. It is therefore an object of the present invention to provide a fluid sensor having improved reliability and lifespan and which is easy and cheap to operate.

SUMMARY OF THE INVENTION

To this end, the invention provides a self-powered in-pipe fluid meter and a fluid transmission piping network as defined in the respective independent claim. Further embodiments of the fluid meter and the piping network according to the present invention are described in the dependent claims.

An aspect of the present invention is the employment of a fluid-driven power source unit such as a hydraulically driven power source unit, which is capable of supplying a continuous supply of electricity to the fluid meter and its associated electrical modules/units. Another aspect is the employment of telemetry, for example, acoustic-wave telemetry, which allows for data transmission to and from the remote fluid sensor/meter without an on-surface module, that is, from inside of the pipe. Both aspects allow the remote flow sensor of the present invention to be a totally in-pipe solution and thereby increase system security and extend the lifespan of the fluid sensor.

Among other fluid sensors, the present invention provides a water quality meter for water distribution networks, wherein a plurality of water quality meters may be embedded within the water pipes of the water distribution network. The plurality of water quality meters can be attached at locations within a pipe in a water transmission & distribution piping network. The water quality meter can detect and measure a plurality of standard or custom parameters that determine the quality of water, and can transmit data to a host terminal without the aid of an external power source or an on-surface module such as an antenna or a solar cell unit.

According to the invention, a self-powered in-pipe fluid meter comprises at least one sensing unit capable of measuring one or more parameters of the fluid inside of the pipe; a telemetric data transmission unit capable of telemetrically transmitting data including a measured fluid parameter to a host terminal and/or another fluid meter; and at least one fluid-driven power source unit capable of generating power from the fluid flow within the pipe and supplying power to the sensing unit and/or the transmission unit.

The self-powered in-pipe fluid meter can be mounted inside of a pipe carrying a fluid therein. In other words, the fluid meter according to the present invention can be mounted on the pipe so as to be entirely embedded in the pipe. The fluid can be a liquid or liquid mixture, a gas or a gas mixture, or a gas/liquid mixture. For example, the fluid can be water or a mixture containing water. The tube can be made of any material suitable for the fluid to be carried therein. For example, if the fluid is water, the tube may be made of metal. However, the tube may be also made of a synthetic material or of glass. Further, the tube can be also made of a transparent material.

For example, the fluid sensor can be a sensor for measuring fluid flow in the tube and/or a sensor for determining the pH-value of the fluid and/or the concentration of a substance within the fluid.

For example, the fluid-driven power source unit can comprise one or more turbine blades (such as a hydro turbine in the case of a water meter), a transmission shaft connected to the turbine blades, and a power generator/alternator. For example, the fluid-driven power source unit can further comprise a battery storage. For example, the fluid-driven power source unit can further comprise a charge controller, a diversion load, and a voltage regulator.

For example, the telemetric data transmission unit can use acoustic waves or electromagnetic waves (such as optical waves) to telemetrically transmit data/signals to the host terminal and/or to another fluid meter. For example, the telemetric data transmission unit can transmit data via an acoustic wave or an electrical wave through the fluid within the pipe, wherein in the case of a liquid such as water or oil acoustic telemetry is preferred because acoustic waves are capable of traveling over a long distance in the pipes (such as metallic pipes). However, the telemetric data transmission unit does not need to transmit the data/signals through the fluid inside the pipe but can also transmit data outside of the pipe, that is, through the medium surrounding the pipe.

In operation, for example, the sensing unit measures/detects one or more fluid parameters of a sample of the fluid within the pipe, and then forwards the measured parameters to the telemetric data transmission unit which transmits the data to a host terminal or another fluid meter. For example, both the sensing unit and the transmission unit are driven by the power source unit, that is, are supplied with power generated by the power source unit from the fluid flow inside the pipe.

The fluid meter according to the present invention allows for a total in-pipe implementation of the entire fluid meter, that is, the fluid meter can be entirely mounted within the pipe without having any on-surface parts (parts being located outside of the pipe such as an antenna or a solar cell unit). For example, the fluid meter can be fixed to the inner surface of the tube by gluing, screwing or via a plug-in connection. Thus, the fluid meter does not need to be protected against damages, for example caused by extreme environmental conditions, and does not need to be regularly surveilled, thereby improving security and lifetime as well as reducing maintenance cost for the fluid meter. Further, the fluid meter according to the present invention can be implemented as a totally self-powered fluid meter not being dependent from any external power source. In other words, the fluid meter can be operated without the aid of an external power source so that it can also be used at isolated places. Further, since the fluid meter uses the fluid flow of the fluid in the pipe, that is, the energy of the fluid, the fluid meter does not have to be accessed or removed from the pipe once it has been installed therein. Thus, the fluid meter according to the present invention is also reliable as well as easy and cheap to operate.

For example, the transmission unit of the fluid meter according to the present invention can have a two-way telemetry function so that it is not only capable of transmitting but also capable of receiving data from the host terminal and/or another fluid meter. For example, parameters/programs of the sensing unit and other units can be updated via the host terminal.

For example, the fluid meter can further comprise at least one fluid sampling unit which takes/extracts a sample of the fluid inside the pipe and exposes/forwards the sample to said at least one sensing unit.

For example, the fluid meter can further comprise at least one signal conditioning unit which processes the fluid parameters measured by said at least one sensing unit.

For example, the fluid meter can further comprise a control unit. For example, the control unit can be capable of controlling power distribution/supply from the power source unit to one or more of the other units, and/or storing data received from said sensing unit and/or the signal conditioning unit and/or the host terminal, and/or processing data received from said host terminal and/or another fluid meter.

DETAILED DESCRIPTION OF ILLUSTRATIVE EMBODIMENTS

Figure 1:
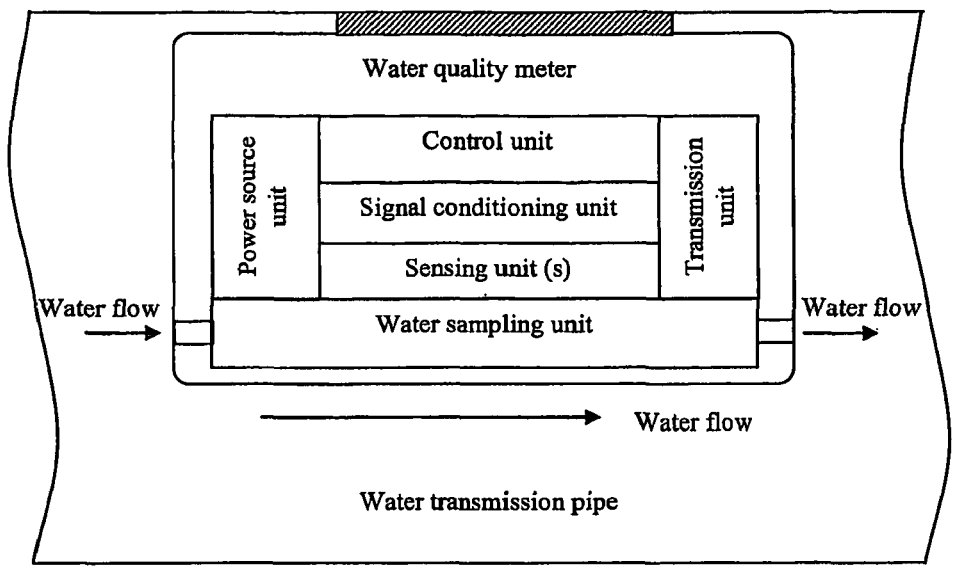
FIG. 1 is a schematic block diagram showing a water quality meter according to an embodiment of the present invention mounted in a water transmission pipe.
Figure 3:
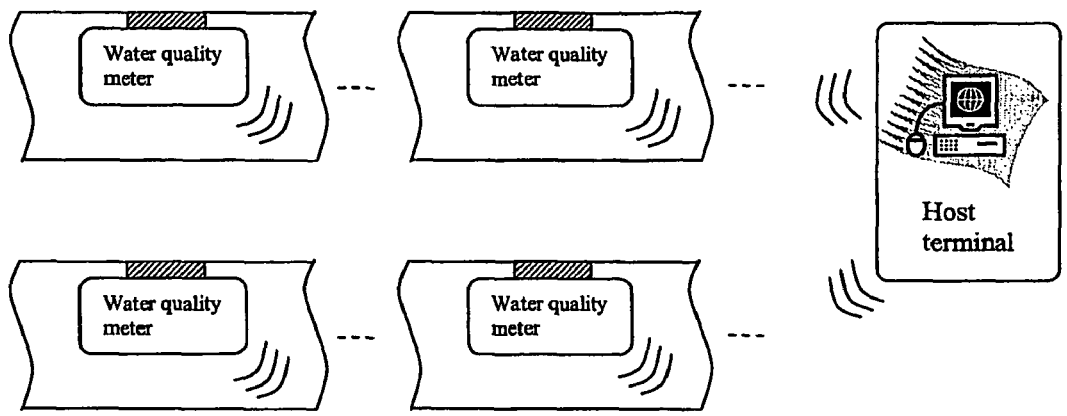
FIG. 3 shows an example of mounting a plurality of water quality meters of the present invention in a water transmission piping system.

FIG. 1 shows a schematic block diagram of a water quality meter according to an embodiment of the present invention. The water quality meter is mounted on the inner side of a water transmission pipe. As can be seen in FIG. 3, a plurality of water quality meters of the present invention can be provided in a water transmission piping system, communicating with one or more host terminals. The water quality meter according to this embodiment comprises a water sampling unit, a sensing unit, a signal conditioning unit, a control unit, a power source unit and a transmission unit. The sampling unit extracts/takes a sample from water flowing inside the water transmission pipe and forwards/exposes the sample to the sensing unit. The sensing unit measures several parameters such as the pH-value and forwards the measured parameters to the signal conditioning unit which processes the measured parameters. The processed parameters are then stored in the control unit and send to a host terminal or another water quality meter via the transmission unit.

Figure 2:
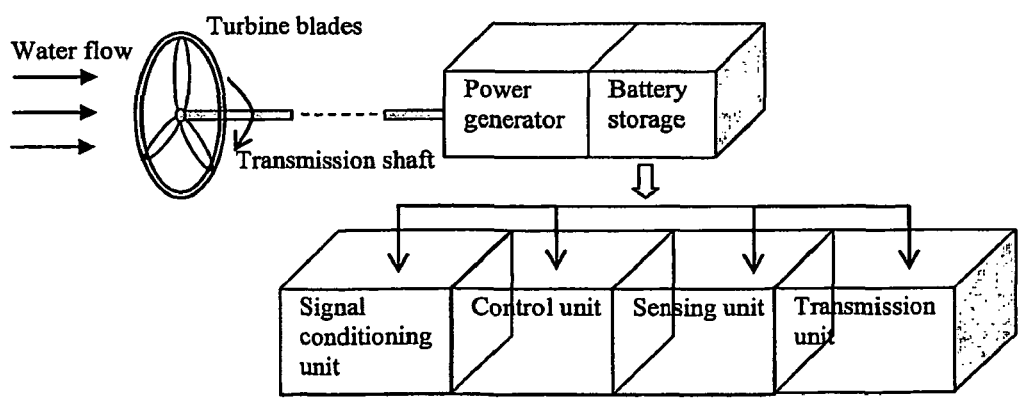
FIG. 2 is a schematic block diagram showing the hydraulic-driven power source unit of the water quality meter shown in FIG. 1.

As can be seen in FIG. 2, the sensing unit, the signal conditioning unit, the control unit, and the transmission unit (as well as the sampling unit) are respectively supplied with electric power by the power source unit. The water/hydraulically driven power source unit comprises turbine blades connected to a transmission shaft. The transmission shaft is connected to and operates an alternator/generator to generate electric power when water causes the blades to rotate. The alternator is connected to a battery storage supplying the different units with electric power.

Figure 4:
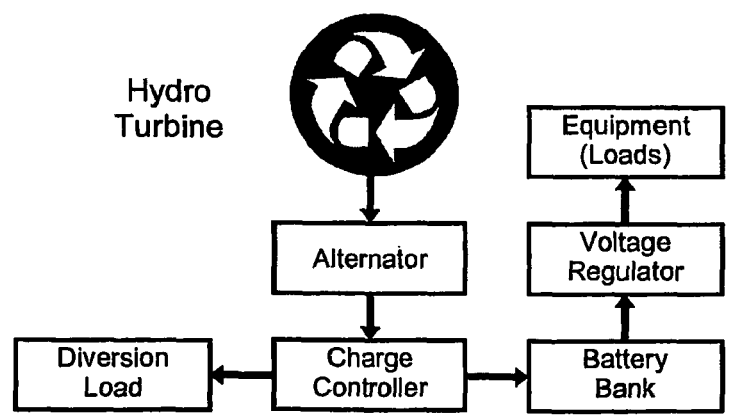
FIG. 4 is a diagram of an embodiment of a hydraulic-driven power source unit of a water quality meter according to the present invention.

FIG. 4 is a diagram of another hydraulic-driven power source unit of a water quality meter according to the present invention, the power source unit comprising:

Hydro Turbine

Water/Hydro turbines generate very reliable power with a very simple design. Typically, a "runner" or propeller is attached to a shaft, which is connected to and operates an alternator to generate electric power when water causes the runner to rotate. There are several types of turbines, but generally they may be classified under three major types: (i) impulse turbines, (ii) reaction turbines and (iii) submersible propeller turbines. Each type of turbine is ideally suited for a different type of water supply. No matter what the source of the running water present on-site, as long as there is a constant supply of flowing of water, there is most likely a water turbine well-suited to provide electricity.

Diversion Load

Hydro turbines are 'active' power producers. When the water is flowing and the turbine is spinning, the hydro turbine is producing electricity. The electricity must be consumed or directed somewhere. Otherwise, the electricity will be converted to heat within the turbine and damage the turbine. In a 'balanced' situation, all of the electricity generated by the hydro turbine is consumed by the electrical loads (that is, by the other units of the water meter such as the transmission unit or the sensing unit) and the recharging of the battery. However, when the battery is fully charged, an excess amount of electricity is produced by the hydro turbine. The function of the Diversion Load is to provide an outlet for this excess power. It is important that the Diversion Load is sized to utilize all of the power produced by the hydro turbine in case there are no electrical loads and the battery is fully charged.

Charge Controller

The Charge Controller charges the Battery Bank and shunts the excess power (not used by the electrical loads and battery charging) to the Diversion Load. The Charge Controller must have sufficient capacity to handle the Battery Bank and entire diversion load.

Batteries

Batteries are an integral part of the self-sufficient energy system. One of the benefits of hydro systems is that fewer batteries are required than with wind or solar systems because of the reliability of hydropower on a day-to-day basis. Furthermore, the amount of energy in the batteries is not dependent on the ever-changing weather. Storage batteries come in many different styles and sizes, but all of them can charge and discharge repeatedly for years.

Voltage Regulator

The Voltage Regulator converts the battery voltage (normally 12V, 24V or 48V) into the single or multi output voltages to meet the main system requirements.

For total in-pipe water quality monitoring system, the data transmission between the monitoring points (nodes), that is, the water quality meters shown in FIG. 3, and the central server can make use of the water distribution pipe. An acoustic telemeter (modem) presents a good solution for data transmission in a water pipe.

An acoustic modem is used for underwater data communication. It converts digital data into special underwater sound signals that can be transmitted in water. The remote receiving modem receives a sound signal and translates it into digital data. Either time domain or frequency domain filtering algorithms may be used to separate the data from the receiving sound signals. The signal range may be, but is not limited to, between about 1,000-about 10,000 meter, and the high speed acoustic modem data rate may be, but is not limited to, more than about 30 kbps.

However, usually acoustic modems are used in open-seas or in open water. In comparing the data transmission of an in-pipe application to that of an open water application, the following issues can be considered:

Sound signal reflection in pipes may cause "echo" at the receiver modem, and this may not happened in an open sea. Accordingly, any resulting "echoes" may be handled by special filtering techniques at the receiver end.

The signal can be transferred along the pipe. As such, the direction of the transmission/reception, as well as the beam width of the transducer can affect the transmission distance and efficiency.

The water distribution pipe may not be straight. The signal behaviour around the bend portion of pipe should be taken into consideration.

Signal reflection in pipe may reduce the signal strength significantly. As such, determining a suitable distance between modems, in both straight pipes or around the bends of pipes may be useful.

If the pipeline is quite long, a signal relay can be used. Each modem may function as a sender/receiver for the host water quality meter, and as a repeater for the signals between the central server and other water quality meters. The selection of the installation location of the water quality meter may take any detection point requirements as well as data transmission requirements into consideration.

(1) Modem with sweep-spread-carrier (S2C) technology

Most of the underwater acoustic modems achieved rather good performance in vertical or direct-path underwater channels, but very poor performance working in horizontal multipath channel. There is a report of investigation of acoustic modem using in horizontal drill pipe filled with mud, the experiment is still carrying out. The preliminary experiment shows the good results, the transmission distance could be 600-1000 meters. With the technology of sweep-spread-carrier (S2C) communication, the signal is carried by a succession of sweeps (permanent and rapid frequency variation) and the receiver modem would separate the multipath arrivals by converting their time delays into their reallocations. When converting the signal into constant intermediate frequencies, the best suitable multipath arrival can be separated in frequency domain by means of conventional frequency filtering. An intricate (multipath) received signal can be simplified to one single arrival by suppressing the interfering components through filtering. Each multipath signal, arriving with its individual time delay to receiver, will have its own instant frequency, which significantly differs from instant frequencies of all other multipath arrivals. This appears to indicate that the acoustic modem with S2C technology would be able to use in water pipe data transmission to extract the data from multipath "echo" in pipe, and also be able to separate the signals from different modem.

(2) Message Transmission Direction

The beam width of transducer may be in certain angles (e.g. between about 60-about 120 degrees), hemispherical or horizontally omni-directional, for example. In the application of water quality monitoring system, the sensory data can be transferred from the water quality meter to the central server, and the central server may need to send a data acquisition command (e.g. adjust sampling rate) to the water quality meter. For long distribution pipes, the signal can be sent and/or received via a relay between modems. In such a case that may mean that a modem may include the capability to receive data from both directions along the pipe. Accordingly, a horizontally omni-directional modem may be considered for use in the present application.

(3) Message Relay, Reliable and Efficient Communication

The arrangement of the water quality meter may take the user's requirement into consideration. In order to have a reliable and efficient communication of data through long water distribution pipes, the working range of the acoustic modem is also an important factor. If the modem working range is about the distance between two modems, the communication therebetween may not be reliable. If the modem working range is far more than the distance between 2 modems, or can cover the working effective ranges of a few other modems, an unnecessary reception and re-transmission of data may take place. As such, it may be suitable to set the modem working range to be between about 2.2-about 2.7 times of the modem's average working distance (range). Detail analysis shows that the amount of data transmission/reception/re-transmission will not increase significantly over a long distance and with multiple repeaters. Instead, the data may still be expected to be relayed and transmitted to the final destination even if some of the modems (provided not the adjacent modems) along the pipe are not working due to any reason.

(4) Data Transmission Control

In this water quality monitoring system, each node data sampling rate (in seconds, minutes) can be configured, to ensure that any water quality problem found takes place in a near real-time situation. In the event that the data transmission is not completed by the acoustic modem, the data transmission control module in the control unit plays an important role. The major objectives of data transmission control unit include real-time updating of water status to a central server, and reducing the power consumption of the acoustic modem.

The control functions of the data transmission control unit can be as follows:

(a) Time based data transmission, i.e. a minimum data update rate (could be in seconds minutes, hours) can also be configured so that the central server can get regular data update and know the availability of the nodes.
(b) Event driven data transmission—When the measured water quality data exceeds the normal working limit, or shows significant change in certain parameters, warning messages may be created and sent to the central server immediately.
(c) On-demand data transmission—Transmits data immediately to the central server if a command to send water quality data is received from the central server.
(d) The message relay control logic described in above (3)

Above logic would control the measuring data to be transmitted to central server only when necessary, so the data transmission/receiving/retransmission along the pipe would be reduced significantly compared with purely time based data transmission.

According to another embodiment of the invention, a water quality meter comprises:

at least one sensing unit, for measuring various aspects of the water quality parameters;

at least one water sampling unit, for exposing the said sensing unit to water;

a transmission unit for two-way telemetry function, which sends data to and receives data from a host terminal and/or another water quality meter;

at least one signal conditioning unit, for processing measurements from said at least one sensing unit;

a control unit, for storing results from said at least one signal conditioning unit, controlling the power distribution to said units, and for processing data from said host terminal and/or another water quality meter; and at least one power source unit, for generating power from a water flow, distributing controlled power to said units.

According to an aspect of this embodiment, the power source unit can comprise a water-driven power generator and a battery storage.

According to another aspect of this embodiment, said two-way telemetry function is provided by an acoustic-wave transmission device.

For example, a working method of the water quality meter according to this embodiment comprises the steps of:

generating and controlling power available to selected sensing unit components;

measuring at least one aspect of the environment in proximity to said sensing unit;

conditioning and storing said at least one measured aspect as data; and, transmitting said data to a host terminal.

To summarize, merits of the present invention include:

(i) In-pipe implementation of the entire fluid meter such as a water quality meter, e.g. including in-pipe signal transmission through the fluid inside the pipe. This generally removes the on-surface parts and ensures good security for the system.

(ii) Self-powered implementation of the entire fluid meter, which improves the reliability and robustness of the system due to its isolation from external environment.

What is claimed is:

1. A self-powered in-pipe water quality meter to be mounted inside of a pipe carrying water or a mixture containing water as a fluid therein, comprising:
   at least one sensing unit configured to measure one or more water quality parameters of the fluid inside of the pipe;
   a telemetric data transmission unit configured to telemetrically transmit data including a measured water quality parameter to a host terminal and/or another fluid meter; and
   at least one fluid-driven power source unit configured to generate power from the fluid flow within the pipe and supplying power to the sensing unit and/or the transmission unit; and
   at least one battery storage charged by the fluid-driven power source;
   wherein the at least one sensing unit is configured to extract a sample of the fluid inside the pipe and expose the sample to said at least one sensing unit.

2. The fluid meter according to claim 1, wherein:
   the transmission unit has a two-way telemetry function so that it is further configured to receive data from the host terminal and/or another fluid meter.

3. The fluid meter according to claim 1, further comprising:
   at least one signal conditioning unit configured to process the fluid parameters measured by said at least one sensing unit.

4. The fluid meter according to claim 1, further comprising a control unit configured to:
   control power supply from the power source unit to one or more of the other units; and/or store data received from said sensing unit and/or at least one signal conditioning unit and/or the host terminal; and/or
   process data received from said host terminal and/or another fluid meter.

5. The fluid meter according to claim 1, said fluid-driven power source unit comprising a power generator and a battery storage.

6. The fluid meter according to claim 1, said transmission unit comprising an acoustic-wave transmission device configured to transmit data via an acoustic wave through the fluid within the pipe.

7. The fluid meter according claim 1, wherein the at least one fluid-driven power source further comprises a diversion load providing an outlet of excess power, when the battery storage is fully charged.

8. A fluid transmission piping network comprising a plurality of self-powered in-pipe fluid meters according to claim 1 respectively mounted inside of a pipe of the piping network.

9. The fluid transmission piping network according to claim 8, each fluid meter being configured to communicate with an adjacent fluid meter via the respective telemetric data transmission unit.

* * * * *